(12) United States Patent
Soto

(10) Patent No.: US 11,525,787 B2
(45) Date of Patent: Dec. 13, 2022

(54) PRE-FILLED PARENTERAL DRUG INSPECTION STATION AND METHOD OF USING THE SAME

(71) Applicant: Manuel Soto, Caguas, PR (US)

(72) Inventor: Manuel Soto, Caguas, PR (US)

(*) Notice: Subject to any disclaimer, the term of this patent is extended or adjusted under 35 U.S.C. 154(b) by 85 days.

(21) Appl. No.: 17/203,980

(22) Filed: Mar. 17, 2021

(65) Prior Publication Data
US 2021/0293725 A1 Sep. 23, 2021

Related U.S. Application Data

(60) Provisional application No. 62/991,058, filed on Mar. 17, 2020.

(51) Int. Cl.

| | |
|---|---|
| *G01N 21/00* | (2006.01) |
| *G01N 21/88* | (2006.01) |
| *G01N 21/59* | (2006.01) |
| *G01N 21/90* | (2006.01) |
| *G01N 33/15* | (2006.01) |
| *G01N 35/00* | (2006.01) |

(52) U.S. Cl.
CPC ......... *G01N 21/8851* (2013.01); *G01N 21/59* (2013.01); *G01N 21/90* (2013.01); *G01N 33/15* (2013.01); *G01N 35/0099* (2013.01); *G01N 35/00594* (2013.01)

(58) Field of Classification Search
CPC .... G01N 21/8851; G01N 21/59; G01N 21/90; G01N 33/15; G01N 35/00594; G01N 35/0099; G01N 21/9027; B07C 5/36; G05B 2219/40609; G05B 2219/45066; B25J 9/1679
USPC ....................................................... 356/440
See application file for complete search history.

(56) References Cited

U.S. PATENT DOCUMENTS

| | | | |
|---|---|---|---|
| 2010/0097465 A1* | 4/2010 | Osborne | ............... A61J 1/2096 340/618 |
| 2017/0027818 A1* | 2/2017 | Tribble | ..................... A61J 1/10 |

* cited by examiner

Primary Examiner — Md M Rahman
(74) Attorney, Agent, or Firm — Hoglund & Pamias, PSC; Roberto J. Rios

(57) ABSTRACT

The invention is a flexible and configurable inspection system for the inspection of container units that combines and integrates a holding assembly for multiple containers integrating servo-controlled rotation of the units, transport and positioning of the containers that simulate human handling, and camera stations employing automated vision inspection. The system performs horizontal inspection for particulate and any other container defect that promotes particulate to better locate within the inspection area of the cameras. Inspection sequences and product recipes combine the typical manual inspection agitation with automated inspection rotational techniques to optimize detection. The system allows for semi-automatic operation with the operator at the front of the station feeding and out-feeding material manually or fully automated with conveyance system feeding and out-feeding material from the back of the station.

19 Claims, 15 Drawing Sheets

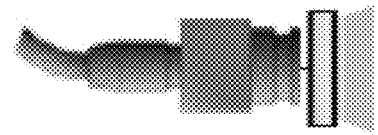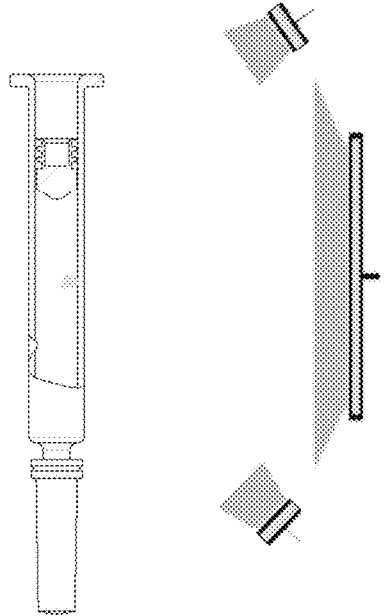
FIGURE 11
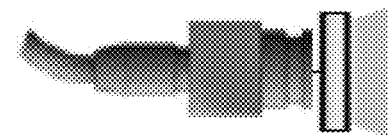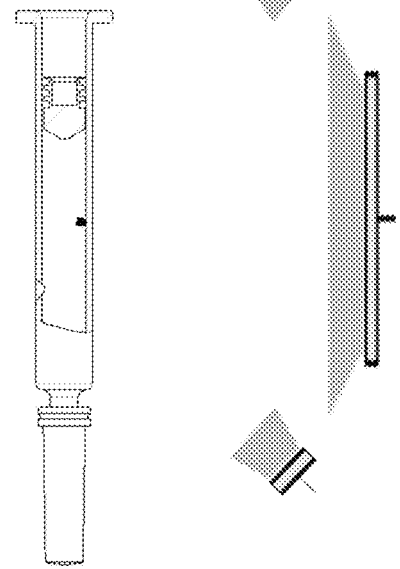
FIGURE 10
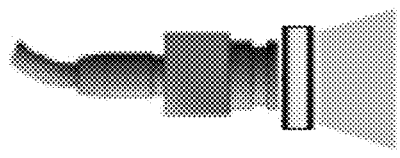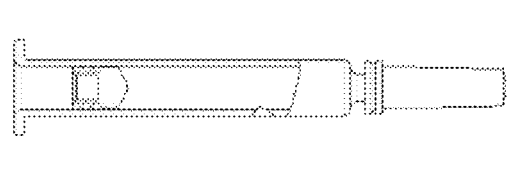
FIGURE 9

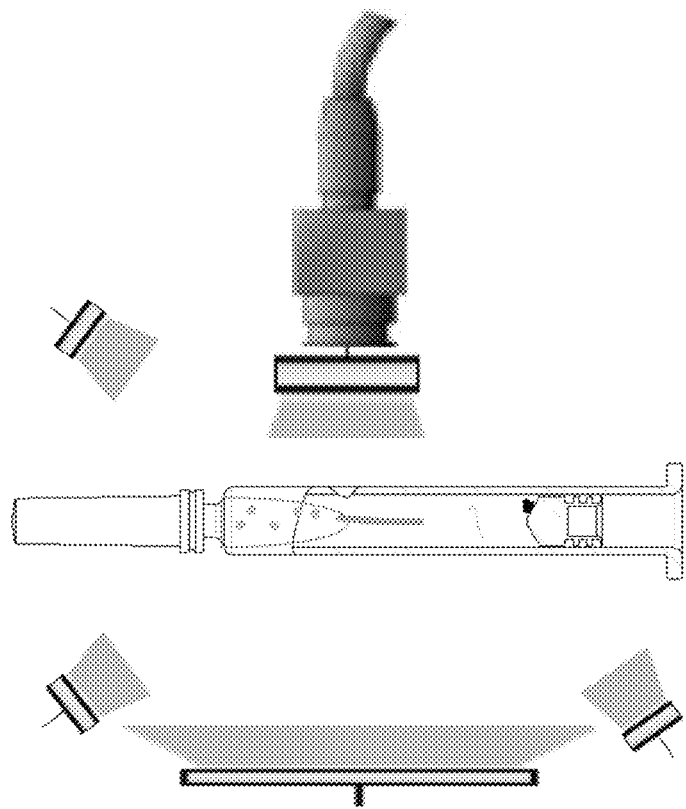
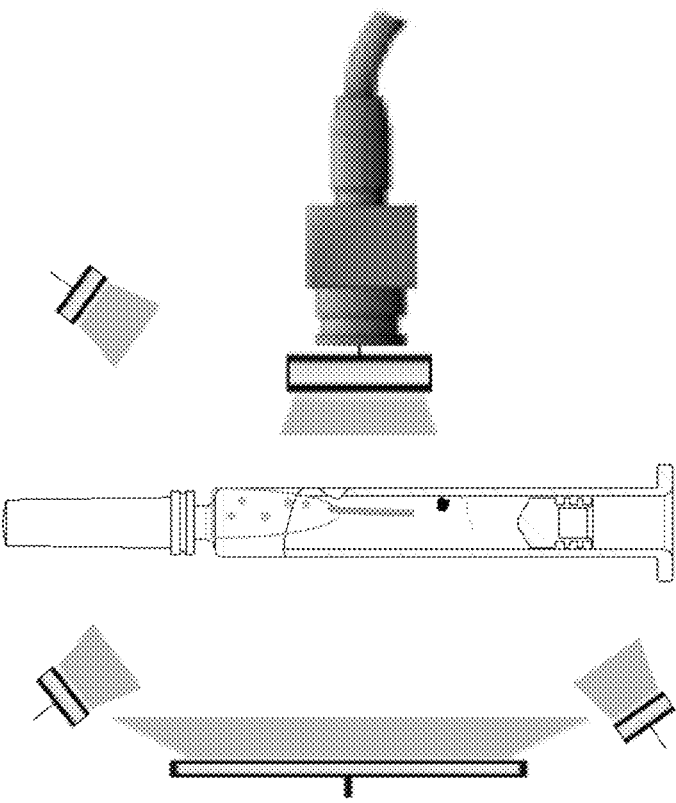

| # | Inspection Position ||||  Illumination Settings (Intensity, Strobe Frequency) |||| Spin Range (RPM) | Tigger Parameters || Stage Time (s) | Reject Bin | Insp. Model or File |
|---|---|---|---|---|---|---|---|---|---|---|---|---|---|---|
| | X | Y | Z | Angle | Front Light | Back Light | Front-Angled Light | Rear-Angled Light | | Period | Exposure | | | |
| 1 | 200 | 250 | 250 | 0 | 0 | 1 | 0 | 0 | 300 | 50 | .1 | 1 | 3 | HOR-A |
| 2 | 200 | 250 | 250 | 0 | 0 | 0 | 1 | 1 | 300 | 50 | .1 | 1 | 3 | HOR-R |
| 3 | 200 | 250 | 250 | 90 | 0 | 1 | 0 | 0 | 0 | 50 | .1 | 1 | 3 | Sub-A |
| 4 | 200 | 250 | 250 | 90 | 0 | 1 | 0 | 0 | 300 | 50 | .1 | 1 | 3 | Fill |
| 5 | 200 | 250 | 200 | 90 | 0 | 1 | 0 | 0 | 300 | 50 | .1 | 1 | 3 | NShld |
| 6 | 200 | 250 | 250 | 90 | 0 | 1 | 0 | 1 | 1000 | 50 | .1 | 1 | 3 | Body |
| 7 | 200 | 250 | 250 | 90 | 0 | 1 | 0 | 1 | 4500 | 50 | .1 | 1 | 3 | CSpin |
| 8 | 200 | 250 | 250 | 90 | 0 | 0 | 1 | 1 | 3500 | 50 | .1 | 1 | 3 | Sub-A |
| 9 | 200 | 250 | 300 | 90 | 0 | 1 | 1 | 0 | 1000 | 50 | .1 | 1 | 3 | PSide |
| 10 | 200 | 250 | 300 | 60 | 0 | 1 | 1 | 0 | 1000 | 50 | .1 | 1 | 3 | PTop |
| 11 | TBD | TBD | TBD | TBD | TBD | TBD | TBD | TBD | 0-5000 | TBD | TBD | 1–10 | TBD | TBD |
| 12 | TBD | TBD | TBD | TBD | TBD | TBD | TBD | TBD | 0-5000 | TBD | TBD | 1–10 | TBD | TBD |
| 13 | TBD | TBD | TBD | TBD | TBD | TBD | TBD | TBD | 0-5000 | TBD | TBD | 1–10 | TBD | TBD |
| 14 | TBD | TBD | TBD | TBD | TBD | TBD | TBD | TBD | 0-5000 | TBD | TBD | 1–10 | TBD | TBD |
| 15 | TBD | TBD | TBD | TBD | TBD | TBD | TBD | TBD | 0-5000 | TBD | TBD | 1–10 | TBD | TBD |
| 16 | TBD | TBD | TBD | TBD | TBD | TBD | TBD | TBD | 0-5000 | TBD | TBD | 1–10 | TBD | TBD |
| 17 | TBD | TBD | TBD | TBD | TBD | TBD | TBD | TBD | 0-5000 | TBD | TBD | 1–10 | TBD | TBD |
| 18 | TBD | TBD | TBD | TBD | TBD | TBD | TBD | TBD | 0-5000 | TBD | TBD | 1–10 | TBD | TBD |
| 19 | TBD | TBD | TBD | TBD | TBD | TBD | TBD | TBD | 0-5000 | TBD | TBD | 1–10 | TBD | TBD |
| 20 | TBD | TBD | TBD | TBD | TBD | TBD | TBD | TBD | 0-5000 | TBD | TBD | 1–10 | TBD | TBD |
| 21 | TBD | TBD | TBD | TBD | TBD | TBD | TBD | TBD | 0-5000 | TBD | TBD | 1–10 | TBD | TBD |
| 22 | TBD | TBD | TBD | TBD | TBD | TBD | TBD | TBD | 0-5000 | TBD | TBD | 1–10 | TBD | TBD |
| 23 | TBD | TBD | TBD | TBD | TBD | TBD | TBD | TBD | 0-5000 | TBD | TBD | 1–10 | TBD | TBD |
| 24 | TBD | TBD | TBD | TBD | TBD | TBD | TBD | TBD | 0-5000 | TBD | TBD | 1–10 | TBD | TBD |
| 25 | TBD | TBD | TBD | TBD | TBD | TBD | TBD | TBD | 0-5000 | TBD | TBD | 1–10 | TBD | TBD |

FIGURE 27

# PRE-FILLED PARENTERAL DRUG INSPECTION STATION AND METHOD OF USING THE SAME

BACKGROUND OF THE INVENTION

Prefilled parenteral drugs, such as prefilled syringes, are widely used throughout the medical and health industry not only because of its simple straight forward application but because it provides individual dosages reducing the possibility of batch or large scale contamination. However, there are several issues to consider during the manufacturing process of prefilled syringes such as filling and sealing the syringe with the drug and later inspecting the individual syringes for quality and health compliance.

The inspection process for prefilled syringes has been traditionally carried out manually by an operator making the whole process cumbersome and time-consuming for the operator and the manufacturer. While some automation steps have been incorporated lately into the inspection process, there is still a need for a system and a method that integrally combines an automatic inspection process with the interaction of an operator to reduce manufacturing time while increasing quality and health compliance.

SUMMARY OF THE INVENTION

The invention provides a flexible and configurable system for the inspection of containers such as prefilled syringes.

According to an aspect of the invention, the system provides an inspection station including a holding mechanism to simultaneously grab and hold multiple containers. The holding mechanism includes a plurality of individual holding elements that are configured to grab and hold respective individual containers.

According to another aspect of the invention, each holding element is provided with a rotation mechanism configured to individually or simultaneously rotate or spin the containers within said holding element.

According to yet another aspect of the invention, the system integrates servo-controlled rotation, robotic transport and positioning of the container and automated vision inspection employing Deep Learning Artificial Intelligence (AI) technology to simulate human handling of the containers during the inspection process.

According to still another aspect of the invention, the system provides the flexibility of handling multiple containers, the capability and consistency of automated inspection, the defect differentiation capabilities of Deep Learning (AI) technology, more than twice the speed of manual inspection, and offers the combination of high detectability, flexibility, and affordable cost.

BRIEF DESCRIPTION OF THE FIGURES

Further features and advantages of the invention will become apparent from the following detailed description taken in conjunction with the accompanying figures showing illustrative embodiments of the invention, in which:

FIG. 9 illustrates a syringe flange inspection configuration according to an embodiment of the present invention.

FIG. 10 illustrates a particle absorbing inspection configuration with slow rotation in horizontal position according to an embodiment of the present invention.

FIG. 11 illustrates a particle reflecting inspection configuration with slow rotation in horizontal position according to an embodiment of the present invention.

FIG. 16 illustrates a particle on glass and floating particle inspection configuration with the needle facing upward according to an embodiment of the present invention.

FIG. 17 illustrates a particle absorbing inspection configuration with subtraction after spinning and stop according to an embodiment of the present invention.

FIG. 27 shows an exemplary Product Recipe requirement with control parameters according to an embodiment of the invention.

Figure 1:
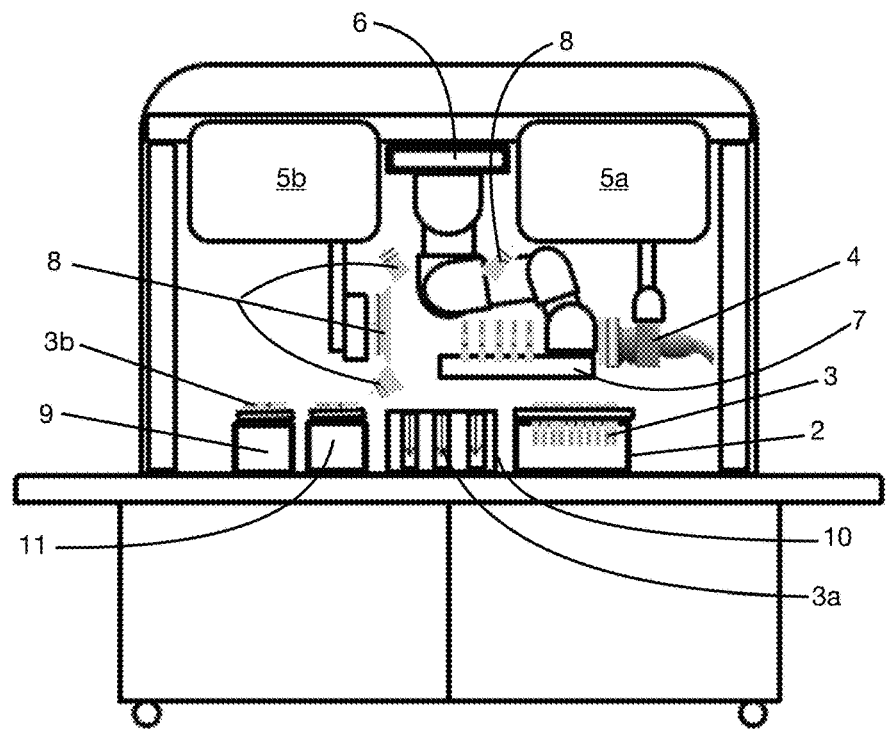
FIG. 1 illustrates a front view of the inspection station according to an embodiment of the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

For the purpose of this description the following terms will be used throughout the description and should be construed and have the below-explained definitions.

"Deep learning" is part of a broader family of machine learning methods based on artificial neural networks. Learning can be supervised, semi-supervised or unsupervised. Artificial Neural Networks (ANNs) were inspired by information processing and distributed communication nodes in biological systems. Deep learning architectures have been applied to fields including computer vision, speech recognition, natural language processing, audio recognition, social network filtering, machine translation, bioinformatics, drug design, medical image analysis, and material inspection, where they have produced results comparable to and in some cases superior to human experts.

"Hardware" is the parts of a computer system, such as the circuit boards, chassis, processors, controllers, enclosures, peripherals, and cables among others that does not include data, software or programs.

Human Machine Interface (HMI) is defined as the software/hardware systems that serve as the interface between operators and the equipment. HMI technology allows operators the ability to control equipment functions.

A parenteral drug is a pharmaceutical drug which its administration is performed by injection, that is, using a hypodermic needle and a syringe, or by the insertion of an indwelling catheter (i.e. Syringes, Vials, and Ampules).

Software is a programmable sequence of steps capable to operate the equipment giving the operator an interface to execute, observe critical parameters and see and correct alarms conditions.

A Product Recipe is a set of parameters and instructions that are processed by a control unit to selectively control movement of the robot arm and the end of arm tool, actuation of the illuminations sources and the cameras to carry out predetermined inspection tests tailored to a specific product's configuration, shape, dimensions and materials. The system provides the functionality to track versions for each of the Product Recipe files, where changes performed to recipe parameters are saved under a new Product Recipe version (i.e., Product-X Rev.01). Each recipe file provides at least 25 configurable inspection stages to allow configuration of the inspection sequence or recipe as exemplified in FIG. 27.

The following abbreviations will be used throughout the description. Admin: System Administrator, AI: Artificial Intelligence, DL: Deep Learning, EoAT: End of Arm Tool (Referring to a Robot end tool), HMI: Human Machine Interface, MVI: Manual Visual Inspection, SME: Subject Matter Expert, upm: Units Per Minute, The system of the present invention is a flexible and configurable station for the inspection of containers such as but not limited to prefilled syringes that combines and integrates three main components: 1) a holding assembly configured to hold multiple containers integrating servo-controlled rotation of the containers similar to high-end automated inspection machines, 2) transportation and positioning of the containers that simulate human handling, and 3) camera stations and a controller employing Deep Learning technology (Artificial Intelligence) to accomplish automated vision inspection. The system is configurable to inspect multiple product-filled containers such as but not limited to syringes, vials, ampules, or cartridges.

Figure 3:
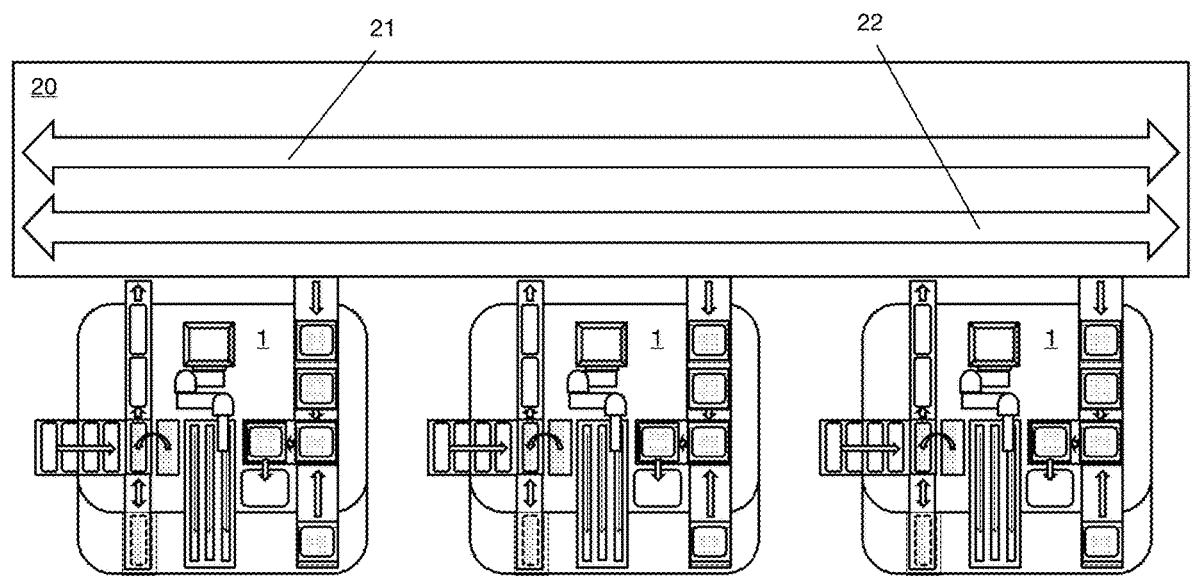
FIG. 3 illustrates an industrial inspection system including the inspection station according to an embodiment of the present invention.

The inspection system and associated method of the present invention provides several novel features. The system performs horizontal inspection for particulate and other container defects. The horizontal inspection position technique promotes particulate movement that is better located within the inspection field of view of the cameras. The inspection sequence according to the invention, combines mechanical agitation (which is similar to the typical manual inspection agitation) with automated inspection rotational techniques to optimize detection. The system allows for modular semi-automatic operation with the operator at the front of the station feeding and out-feeding material manually or a fully automated operation connected to a conveyor highway system (magnetic conveyance system) feeding and out-feeding material fully automated from the back of the station as illustrated in FIG. 3. It also provides a convenient layout that accommodates an automated inspection operation in a similar layout as a manual inspection booth. The system of the present invention facilitates replacement and/or retrofit of the inspection booths stations within a typical manual line layout. In addition, the inspection system of the present invention provides fully integration of deep learning technology for container inspection ensuring strong capability to differentiate defects from good product and enabling optimal performance of the inspection operation.

As previously explained, the present invention is a flexible and configurable system for inspection of containers that integrates servo-controlled rotation of the units, robotic handling and positioning to provide specific tilting and flipping motions of the containers to simulate human handling, and stations with controlled illumination and vision cameras employing Deep Learning (AI) technology to accomplish automated inspection of the product units. The station facilitates inspection of several containers for multiple defects such as but not limited to container components defects, solution color and turbidity, fill level, seal quality, and particles in solution among others.

Figure 2:
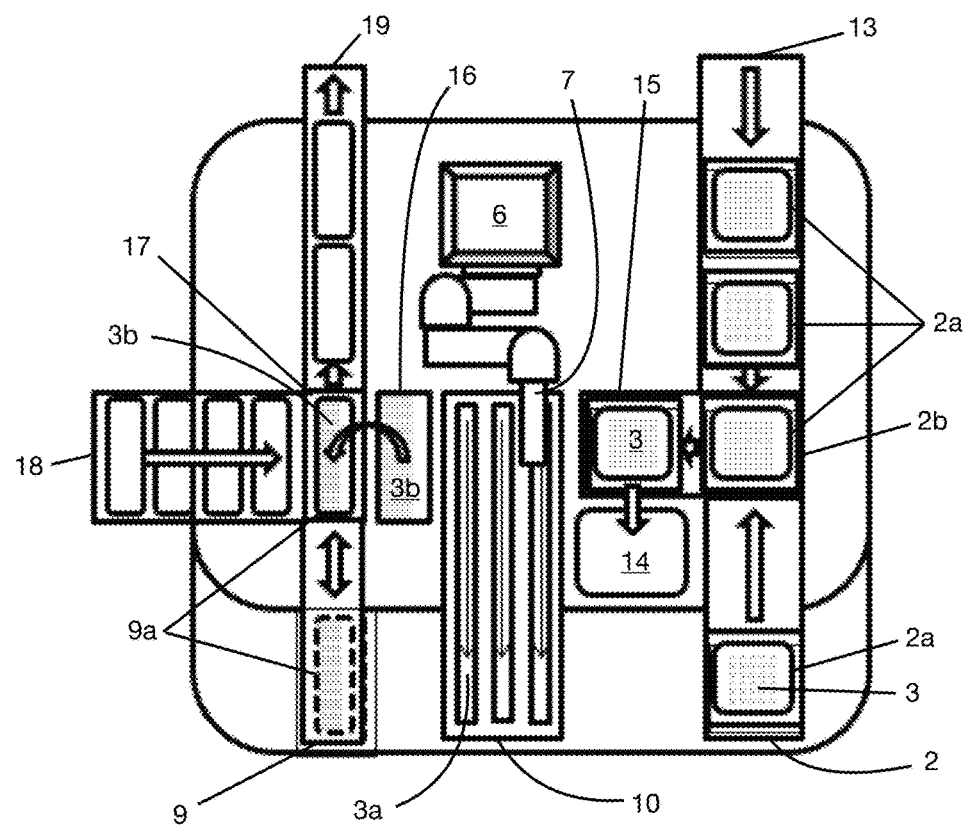
FIG. 2 illustrates a top view of the inspection station according to an embodiment of the present invention.

In general terms, the system and method of present invention involves the following sub-processes.
- Infeed Station to load incoming product onto the inspection stations for pickup and positioning.
- Automated handling, positioning, illumination, and Vision Inspection using Deep Learning technology as the main inspection approach to inspect:
  - Container Components Defects (i.e., Cracks, Chipped, Dirt, Stains, Seal, Malformations, etc.)
  - Product Solution Defects (i.e., Solution Discoloration, Turbidity, Fill Level, etc.)
  - Particulate Defects (Moving, Floating Particles, Heavy Particles, adhered to glass-wall, etc.)
- Pick & Place for sorting/segregation of rejected and accepted units, and re-nesting onto trays FIG. 1 and FIG. 2 illustrate the components according to a preferred embodiment of the inspection station of the present invention.

According to a preferred embodiment, the inspection station 1 includes a NEST loading area 2b for receiving a NEST 2a carrying the plurality of prefilled syringes 3. One important aspect of the invention is that the NESTS 2a can be loaded into the NEST loading area 2b manually by an operator via a manual NEST loading area 2 and/or automatically via a NEST auto-in feed area 13. A unit pickup area 15 is provided adjacent to the NEST loading area 2b for receiving either the prefilled syringes that are ready for inspection or the NEST 2a carrying the prefilled syringes 3 that are ready for inspection. One of the main components of the inspection station 1 is the robot arm 6 coupled to the end of arm tool 7. According to an embodiment, the robot arm 6 is a conventional robot arm comprising a plurality of sections interconnected to allow movement of the arm in any desired direction. As can be appreciated in FIG. 4 and FIG. 5, the end of arm tool 7 of the invention includes a plurality of syringe holding units, wherein each syringe holding unit has a holding element 7a configured to grab a flange 27 of the syringe 3. In addition, the end of arm tool 7 is provided with a rotary element 7b to selectively rotate or spin the syringe 3 in place while being hold by the holding element 7a. It must be noted that the end of arm tool 7 can also rotate horizontally 360°. An empty NEST discharge area 14 is also provided to receive from the unit pickup area 15 empty NESTS 2a after all the prefilled syringes 3 carried by NESTS 2a are transferred so that the empty NESTS can be removed and/or reused for the inspection process. This step can be carried manually by the operator, automatically or a combination thereof.

At least one camera 4 and at least one illumination source 8 are provides as part of s vision station of the inspection system of the invention. In a preferred embodiment, the vision station includes three cameras and 4 illumination sources, but it is envisioned that other amounts can be used. As can be appreciated from the FIG. 1, the cameras and the illuminations sources are positioned in the vision station so that the robot arm 6 with the end of arm tool 7 can freely move, tilt and rotate the prefilled syringes 3.

A syringe rejection area 10 is provided to receive from said end of arm tool 7 any pre-filled syringe 3 that failed the inspection process which can be then removed from the inspection station 1 either manually by an operator or automatically. A separator area 16 is provided to receive from said end of arm tool 7 any pre-filled syringe 3b that passed the inspection process. In addition, a rondo tray loading area 17 is provided to accommodate a rondo tray 9a configured to receive the pre-filled syringes 3b from the separator area 16, wherein he pre-filled syringes 3 can be moved by the end of arm tool 7 or another robot arm. The rondo trays 9a can be loaded into the rondo tray loading area 17 via a manual rondo tray loading area 9 and/or automatically via a rondo auto-outfeed area 19.

The inspection station includes at least one Human Machine Interface (HMI) 5a,5b that provides an operator the following features:
  User account and access management
  Storage of Product Recipe files with version control
  User interface system that includes configurable recipe files for multiple products
  Recipe with configurable inspection sequences for the different stages: corresponding positioning of the syringe units within the cameras' field of view; tilting, flipping, and/or rotation profiles of the units; illumination patterns and parameters; and vision inspection file for each stage
  Touchscreen for HMI navigation, inspection result confirmation, and image labeling
  Storage of labelled images for Deep Learning model(s) generation
  Display of equipment status and batch data
  Data collection counters and display according to inspection results
  Retrieval, display, and print of inspection batch reports
  Audit trail for SME and Admin activities The inspection system of the invention provides material handling and control to bring syringe units into focus within the cameras' field of views. Container unit gripping, tilting and spinning mechanisms are provided with controls to provide the required positioning and rotation to enable configurable inspections of all unit sections. Multiple camera views of the unit sections (i.e., Body of the Container, Seal, Product Solution, etc.) are also provided. Illumination arrays are provided to inspect for light absorbing and reflecting defects.

According to an embodiment of the invention, the inspection station operates in two main production modes: 1) Supervised Production Mode that provides assistance to the operator by performing inspection of container units and displaying the inspected digital images on-screen for the operator to confirm the result and classify and label the image, and 2) Automatic-Mode inspecting mode with Deep Learning Model(s) previously generated (under version control) with the images collected in Supervised Production Mode. Furthermore, the system provides different modes for labeling of images, vision file development, and equipment maintenance.

The inspection station of the invention is configurable to inspect multiple product-filled containers (i.e., Syringes, Vials, Ampules, or Cartridges). The operating sequence of the system is structured in two main sequences: 1) "General Sequence" that controls the in-feed, out-feed, the handling and sorting of the containers, and 2) "Inspection Sequence" that controls the positioning of the units for inspection and defines the inspection files and all image acquisition and testing parameters. The "Inspection Sequence" can be tailored to the specific container according to its components, fill level, and product and container characteristics.

Figure 4:
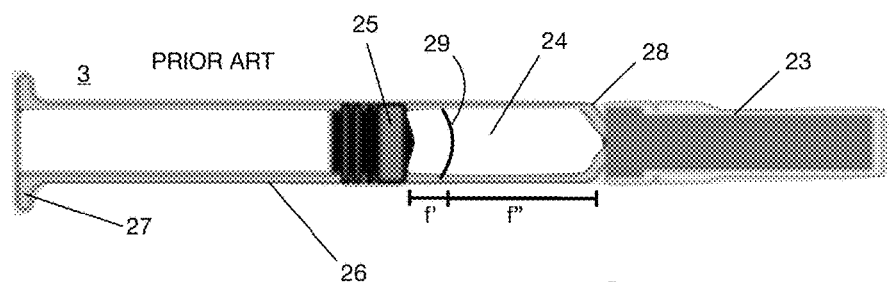
FIG. 4 illustrates an exemplary prefilled syringe to be inspected by the inspection station according to an embodiment of the present invention.

FIG. 4 illustrates an exemplary pre-filled syringe 3 and the associated regions and defects inspected by the inspection station according to an embodiment of the invention. For example, the system detects if the needle shield 23 is displaced, bent or if a needle protrudes from the shield, if the body 26 and flange 27 are cracked, stained, chipped, bruised or scratched, the distance f' between a plunger 25 and a meniscus 29 of a liquid 24 and the distance f" between the meniscus 29 and the shoulder 28 of the syringe.

Figure 5:
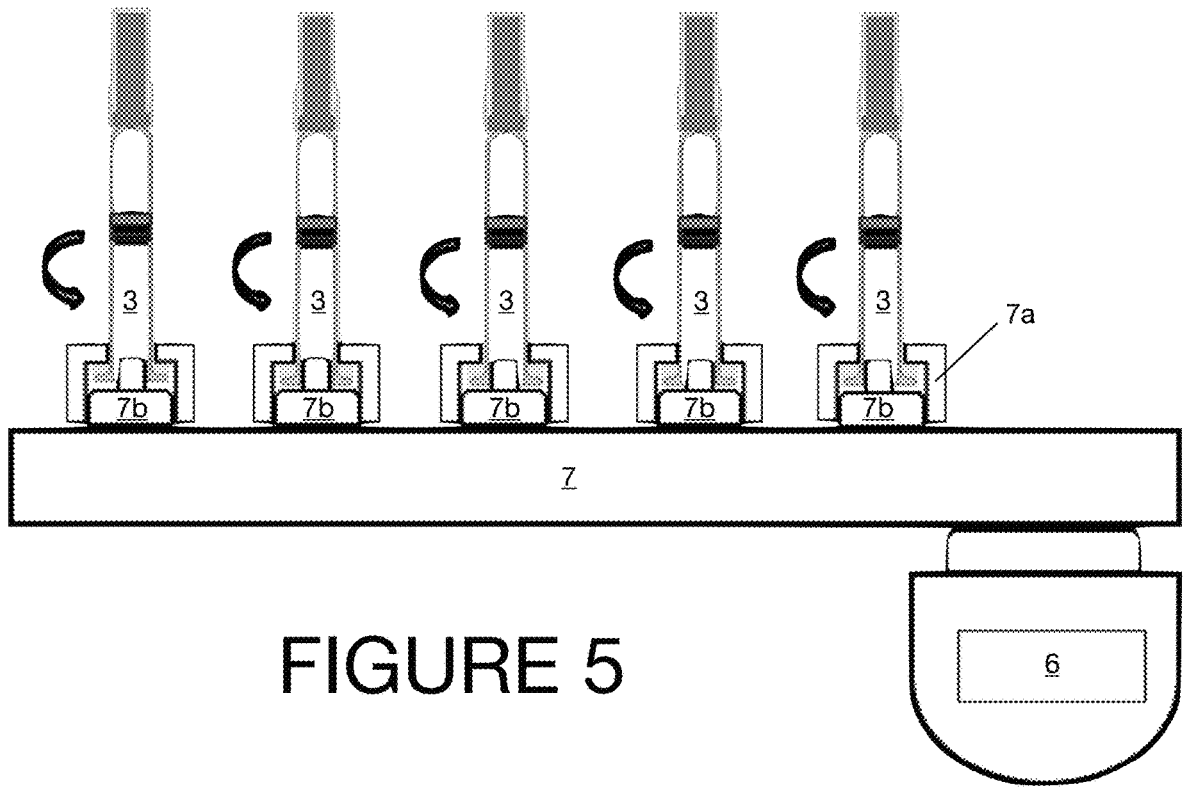
FIG. 5 illustrates an end of arm tool according to an embodiment of the present invention.
Figure 6:
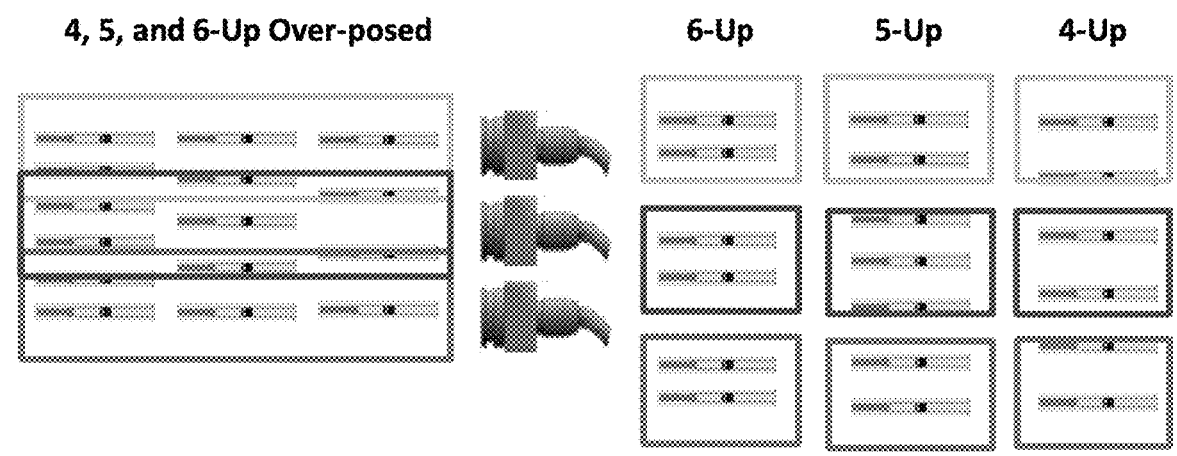
FIG. 6 shows an exemplary camera field of view for the prefilled syringes hold by the end of arm tool according to an embodiment of the present invention.

The end of arm tool 7 according to an embodiment illustrated in FIG. 5, has a quick change-over arrangement that allows changing different parts of the tool like holding grippers 7a based on for example the type and dimension of a syringe Flange and/or a vial Cap, among others. According to an embodiment of the invention, the end of arm tool 7 provides servo spinning of the product units up to 5000 RPM and includes an assembly attached to the robot arm 6 for handling and to provide specific tilting and flipping motions simulating human handling. The end of arm tool 7 can also be changed to accommodate 8, 10, and 12 NEST. The inspection station includes a camera station with preferably 3 cameras so that the total field of view covers the units picked-up by the end of arm tool 7. The field of view of the cameras accommodates for inspection of all syringes on the End of Arm Tool (EoAT) for all formats 4, 5, and 6-Up as illustrated in FIG. 6.

Figure 7:
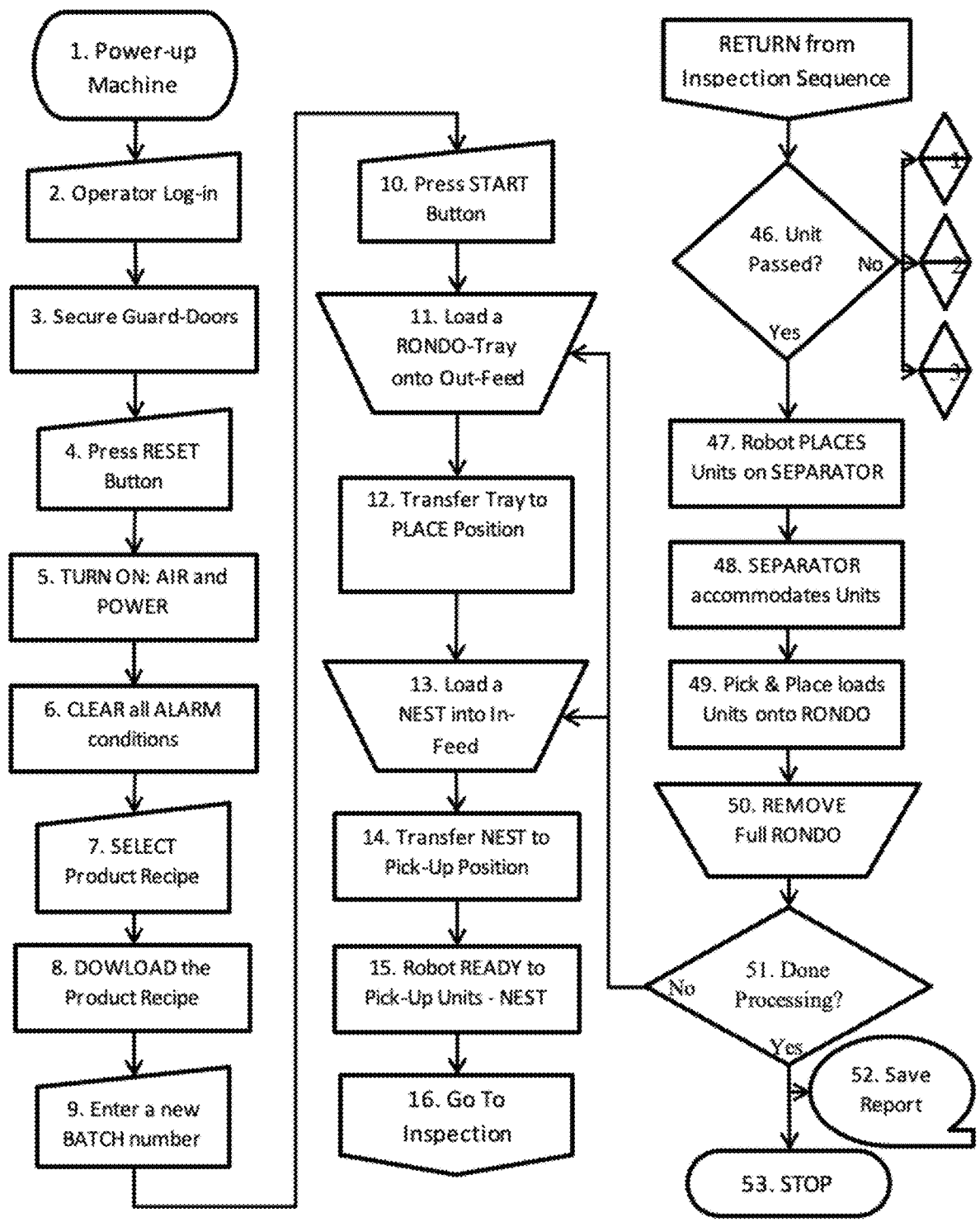
FIG. 7 shows a flowchart explaining the general method of using the inspection station according to an embodiment of the present invention.
Figure 8:
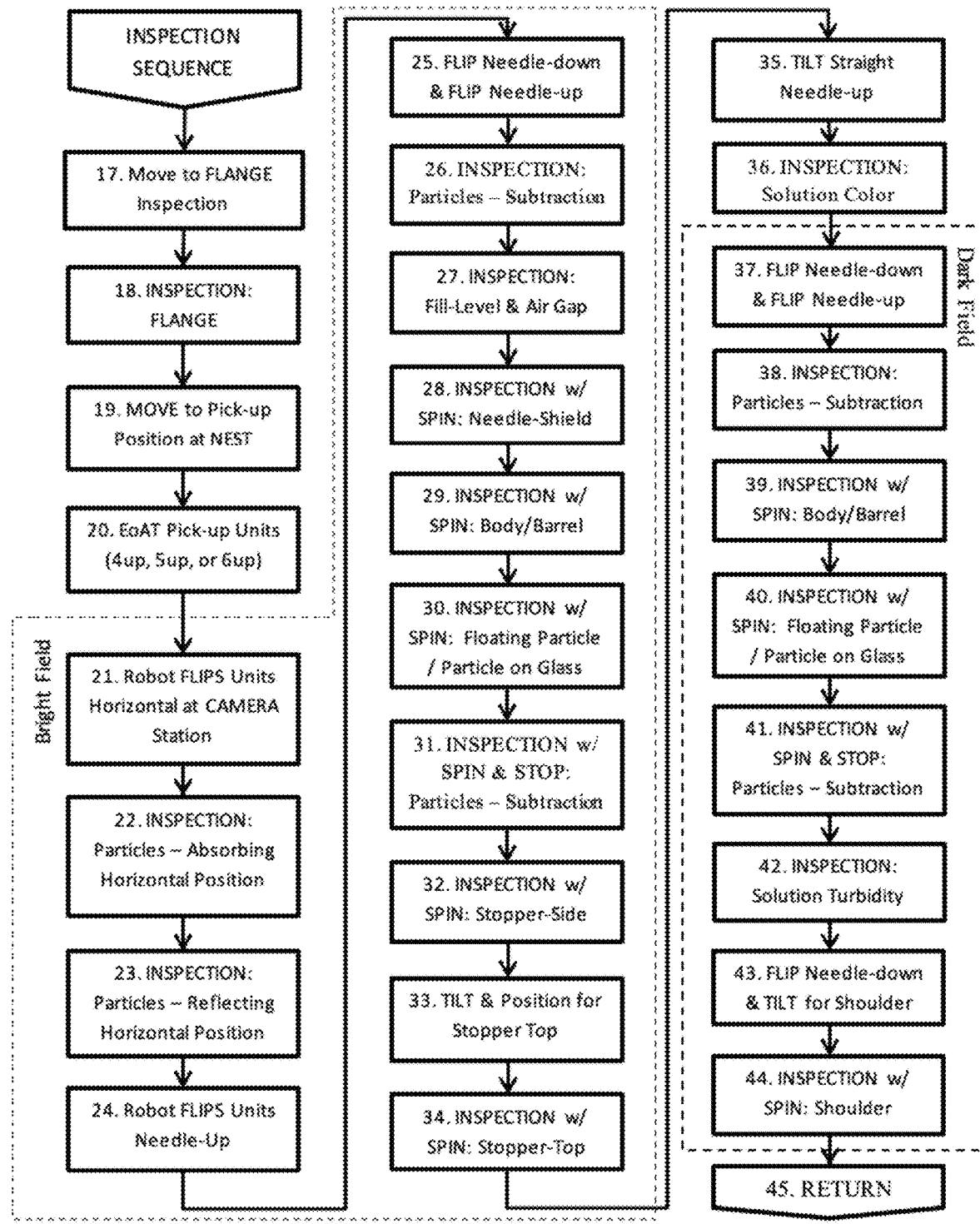
FIG. 8 shows a flowchart explaining an exemplary inspection sequence according to an embodiment of the present invention.

The operation of the inspection station according to an embodiment of the invention, ix explained in Table 2 below and the flowcharts illustrated on FIGS. 7-8.

TABLE 2 sequential steps associated with the inspection of syringes according to an embodiment of the invention.

| Step | Description |
|---|---|
| 1 | Power-up Machine |
| 2 | Operator Log-in into the application |
| 3 | Secure guard-doors |
| 4 | Press the RESET (Button) to turn on compressed air and process power |
| 5 | TURN ON compressed air and power |
| 6 | Clear alarm conditions |
| 7 | Select the PRODUCT RECIPE corresponding the product batch |
| 8 | Download the PRODUCT RECIPE |
| 9 | Enter the new BATCH number |
| 10 | Press START button to initiate the processing of the units |
| 11 | Operator loads a RONDO-Tray into the Out-feed |
| 12 | Operator moves the RONDO-Tray to the PLACE Position This operation could be manual or an automated transfer according the machine options selected |
| 13 | Load a NEST into the In-feed |
| 14 | Operator moves the NEST to the Pick-up position This operation could be a manual move or an automated transfer according the machine options selected |
| 15 | Robot ready to pick-up units from the NEST |
| 16 | Go To INSPECTION SEQUENCE to initiate inspection stages |
| 17 | Move to FLANGE Inspection at the NEST |
| 18 | Inspection for FLANGE: This stage inspects the integrity of the Flange prior to pick-up from the NEST |
| 19 | MOVE to Pick-up position at NEST |
| 20 | EoAT Picks-up Units from NEST (4up, 5up, or 6up according to the NEST format) |
| 21 | Robot FLIPS Units Horizontal at CAMERA Station |
| 22 | INSPECTION at Horizontal Position while SPIN for Light-Absorbing Particles (moving or attached to glass) |
| 23 | INSPECTION at Horizontal Position while SPIN for Light-Reflecting Particles (moving or attached to glass) |
| 24 | Robot FLIPS Units Needle-up |
| 25 | FLIP Needle-down & FLIP back Needle-up to induce movement to the particles suspended in the fluid |
| 26 | INSPECTION for Particles (Light Absorbing) right after flipping motion using Image Subtraction to capture particles moving after the flipping movement |
| 27 | INSPECTION for FILL-LEVEL & AIR-GAP for the units in a static position |
| 28 | INSPECTION while SPIN for Needle-Shield The spin provides multiple views to cover 360deg of the unit |
| 26 | INSPECTION while SPIN for Body/Barrel (Bright Background) The spin provides multiple views to cover 360deg of the unit |
| 30 | INSPECTION while SPIN for Floating Particles and/or Particles on Glass (Bright Background) |
| 31 | INSPECTION with SPIN & STOP for Particles (Light Absorbing) using Image Subtraction after stopping the spinning |
| 32 | INSPECTION while SPIN for Stopper-Side The spin provides multiple views to cover 360deg of the unit |
| 33 | TILT & Position for Stopper Top inspection |
| 34 | INSPECTION while SPIN for Stopper-Top The spin provides multiple views to cover 360deg of the unit |
| 35 | TILT Straight Needle-up |
| 36 | INSPECTION Solution Color for the units in a static position |
| 37 | FLIP Needle-down & FLIP Needle-up |
| 38 | INSPECTION for Particles (Light Reflecting) right after flipping motion using Image Subtraction to capture particles moving after the flipping movement |
| 39 | INSPECTION while SPIN for Body/Barrel (Dark Background) The spin provides multiple views to cover 360° of the unit |
| 40 | INSPECTION while SPIN for Floating Particles and/or Particles on Glass (Dark Background) |
| 41 | INSPECTION with SPIN & STOP for Particles (Light Absorbing) using Image Subtraction after stopping the spinning |
| 42 | INSPECTION for Solution TURBIDITY for the units in a static position |
| 43 | FLIP Needle-down & TILT for Shoulder Inspection |
| 44 | INSPECTION while SPIN for SHOULDER. The spin provides multiple views to cover 360deg of the unit |
| 45 | RETURN to MAIN SEQUENCE |
| 46 | Unit Passed? Decision point to sort units to their corresponding EJECT/REJECT Lane |
| 47 | Robot PLACES Units on SEPARATOR |
| 48 | SEPARATOR accommodates Units with the corresponding spacing ready for placement onto tray |
| 49 | Pick&Place LOADS Units onto RONDO Tray |
| 50 | REMOVE Full RONDO |
| 51 | Done Processing? Decision point to continue loading more material returning to steps 11 and 13 |
| 52 | Save REPORT to close-out BATCH |
| 53 | STOP |

FIG. 9 illustrates a camera configuration for inspecting a condition of a syringe flange inspection (Cracked, Broken, Chipped, Malformed), (Step 18, Table 1). The configuration settings used are:

Camera: 12 MP (Monochrome)
Illumination: Backlight (OFF), Front Light (ON), Rear Angled (OFF), Front Angled (OFF)
Field of View: 2× Flange diameter
# of Images Taken: 1

FIG. 10 illustrates a camera configuration for inspecting the body of the syringe to identify particle absorption in the syringe in horizontal position with slow rotation, (Step 22, Table 1). The configuration settings used are:

Camera: 12 MP (Monochrome)
Illumination: Backlight (ON,Strobe), Front Light (OFF), Rear Angled (OFF), Front Angled (OFF)
Field of View: 1× the syringe barrel length
# of Images Taken: Multiple (+10)

FIG. 11 illustrates a camera configuration for inspecting the body of the syringe to identify light-reflecting particles in the syringe in horizontal position with slow rotation, (Step 23, Table 1). The configuration settings used are:

Camera: 12 MP (Monochrome)
Illumination: Backlight (OFF), Front Light (OFF), Rear Angled (ON,Strobe), Front Angled (ON,Strobe)
Field of View: 1× the syringe barrel length
# of Images Taken: Multiple (+10)

Figure 12:
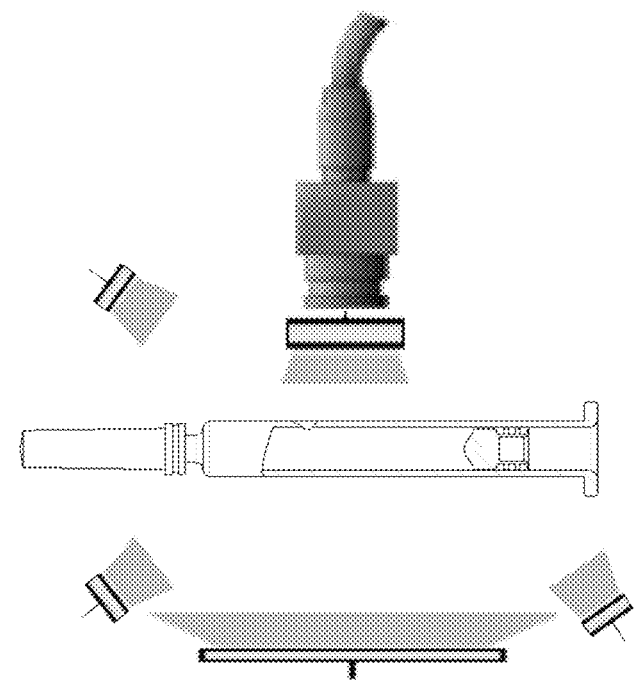
FIG. 12 illustrates a particle absorbing inspection configuration with subtraction after inversion according to an embodiment of the present invention.

FIG. 12 illustrates a camera configuration for inspecting the body of the syringe to identify moving light-absorbing particles in the syringe with a subtraction after inversion, (Step 26, Table 1). The configuration settings used are:

Camera: 12 MP (Monochrome)
Illumination: Backlight (ON,Strobe), Front Light (OFF), Rear Angled (OFF), Front Angled (OFF)
Field of View: 1× the syringe barrel length
# of Images Taken: Multiple (+10)

Figure 13:
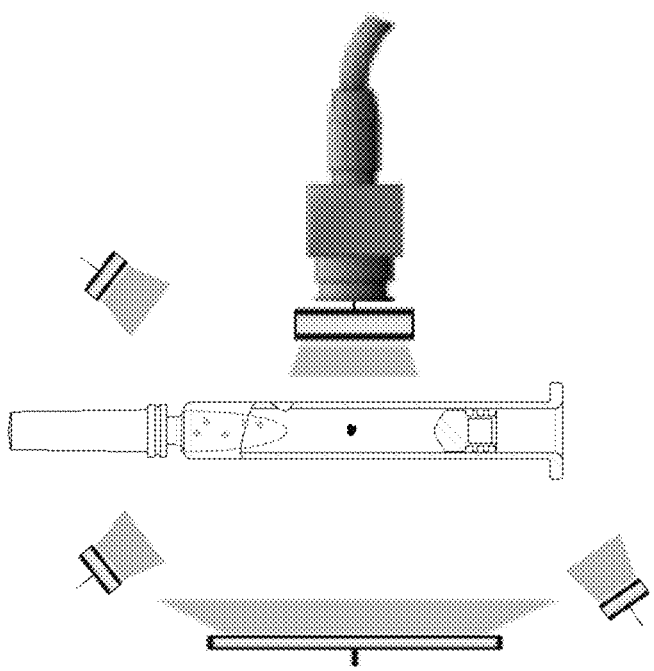
FIG. 13 illustrates a fill level and air gap inspection configuration according to an embodiment of the present invention.

FIG. 13 illustrates a camera configuration for inspecting the body of the syringe to identify the fill level (Distance from Plunger to Meniscus) and the air gap (Distance from Meniscus to Shoulder), (Step 27, Table 1). The configuration settings used are:

Camera: 12 MP (Monochrome)
Illumination: Backlight (ON,Strobe), Front Light (OFF), Rear Angled (OFF), Front Angled (OFF)
Field of View: 1× the syringe barrel length
# of Images Taken: 1

Figure 14:
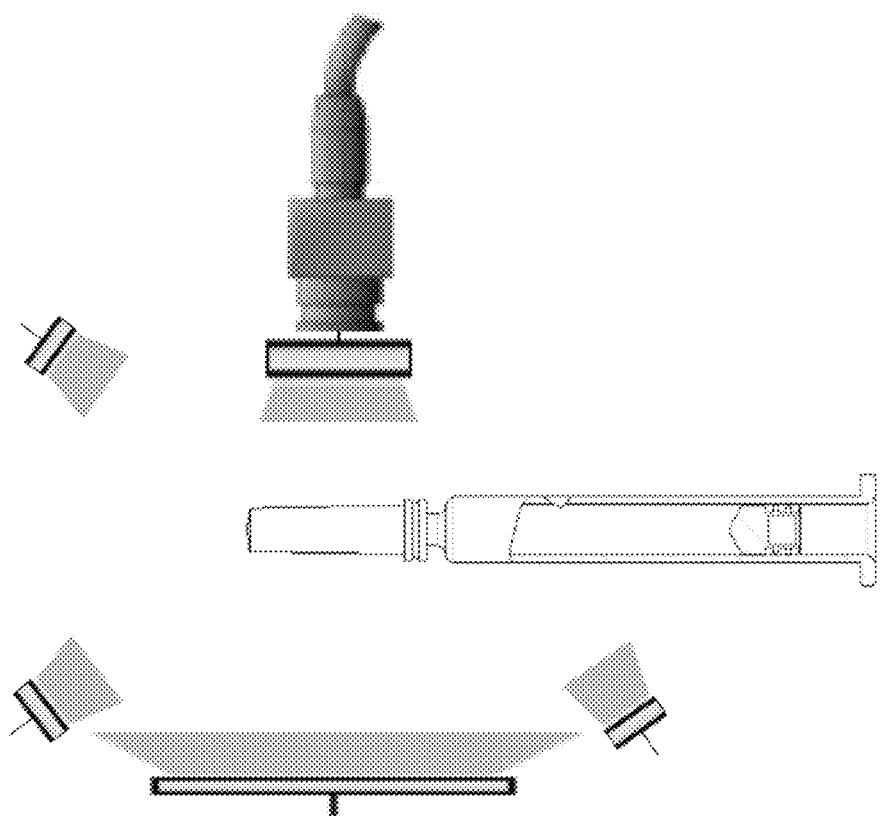
FIG. 14 illustrates a needle shield inspection configuration according to an embodiment of the present invention.

FIG. 14 illustrates a camera configuration for inspecting the needle shield to identify a bent needle, a displaced cover shield, damage on the cover shield and a protruding needle (Step 28, Table 1). The configuration settings used are:
Camera: 12 MP (Monochrome)
Illumination: Backlight (ON,Strobe), Front Light (ON,Strobe), Rear Angled (OFF), Front Angled (OFF)
Field of View: 1× the syringe barrel length
# of Images Taken: Multiple (+10)

Figure 15:
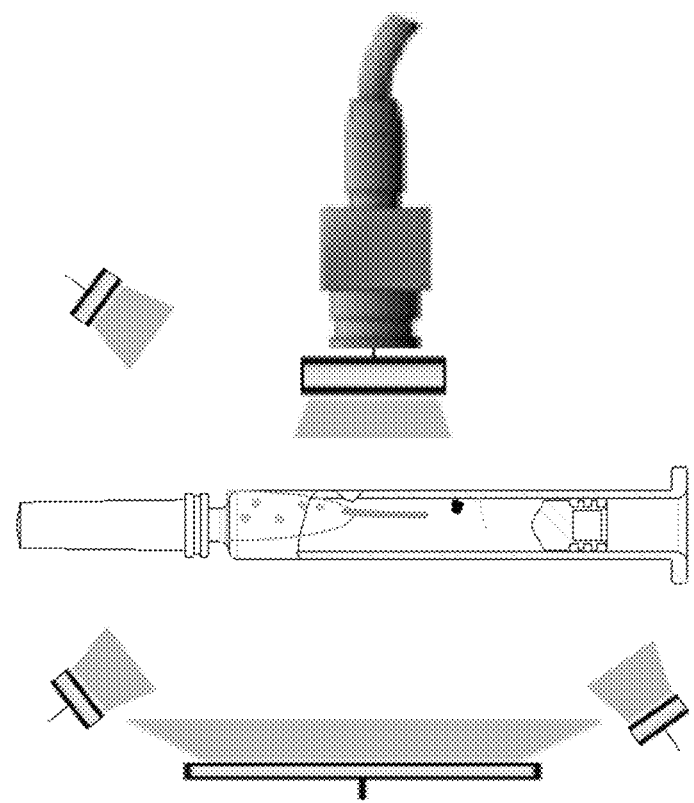
FIG. 15 illustrates a syringe body inspection configuration with the needle facing upward according to an embodiment of the present invention.

FIG. 15 illustrates a camera configuration for inspecting the body of the syringe to identify a crack on the barrel, an airline, a chipped barrel, a scratched barrel, dirt or stain and a bruise (Step 29, Table 1). The configuration settings used are:
Camera: 12 MP (Monochrome)
Illumination: Backlight (ON,Strobe), Front Light (OFF), Rear Angled (ON,Strobe), Front Angled (OFF)
Field of View: 1× the syringe barrel length
# of Images Taken: Multiple (+10)

FIG. 16 illustrates a camera configuration for inspecting the body of the syringe to identify particle in the glass wall of the syringe and any floating particle with a needle up and a high spin (Step 30, Table 1). The configuration settings used are:
Camera: 12 MP (Monochrome)
Illumination: Backlight (ON,Strobe), Front Light (OFF), Rear Angled (ON,Strobe), Front Angled (OFF)
Field of View: 1× the syringe barrel length
# of Images Taken: Multiple (+10)

FIG. 17 illustrates a camera configuration for inspecting the body of the syringe to identify moving light-absorbing particles with spinning and a subtraction after stopping (Step 31, Table 1). The configuration settings used are:
Camera: 12 MP (Monochrome)
Illumination: Backlight (ON,Strobe), Front Light (OFF), Rear Angled (OFF), Front Angled (OFF)
Field of View: 1× the syringe barrel length
# of Images Taken: Multiple (+10)

Figure 18:
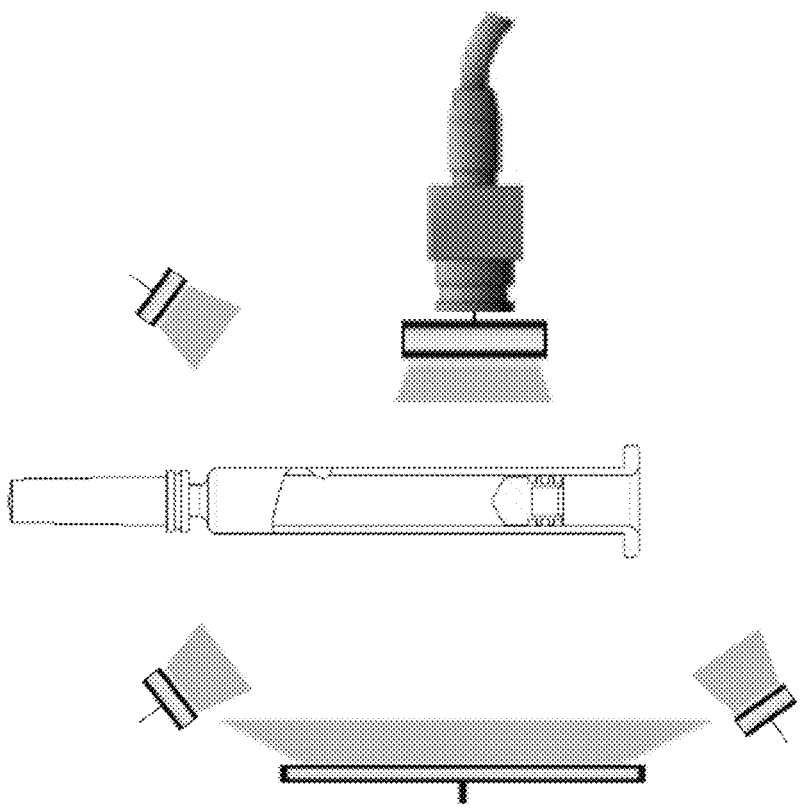
FIG. 18 illustrates a plunger side inspection configuration with spinning according to an embodiment of the present invention.

FIG. 18 illustrates a camera configuration for inspecting the side of the syringe's plunger to identify ribs molding defects, damaged ribs, liquid between ribs, stains on the plunger, an inverted plunger and a misaligned plunger (Step 32, Table 1). The configuration settings used are:
Camera: 12 MP (Monochrome)
Illumination: Backlight (ON,Strobe), Front Light (ON,Strobe), Rear Angled (OFF), Front Angled (OFF)
Field of View: 1× the syringe barrel length
# of Images Taken: Multiple (+10)

Figure 19:
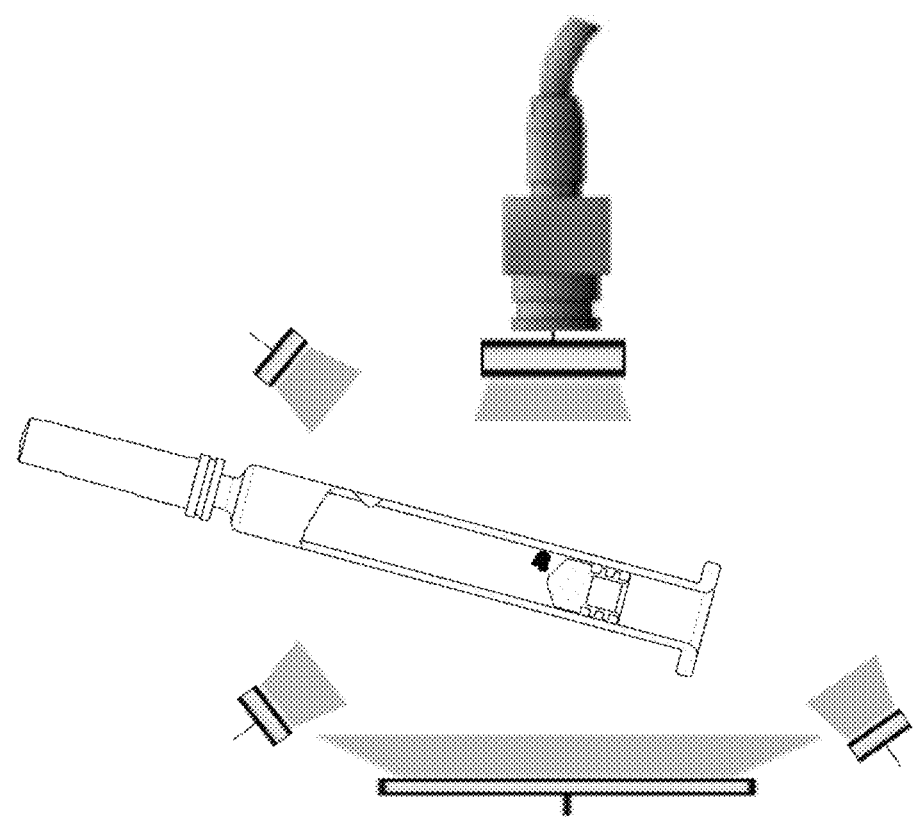
FIG. 19 illustrates a plunger top inspection configuration with tilting and spinning according to an embodiment of the present invention.

FIG. 19 illustrates a camera configuration for inspecting the top of the syringe's plunger to identify Stains on Dome, Specks, Protruding Particles and Heavy Particles (Step 34, Table 1). The configuration settings used are:
Camera: 12 MP (Monochrome)
Illumination: Backlight (ON,Strobe), Front Light (OFF), Rear Angled (OFF), Front Angled (ON,Strobe)
Field of View: 2× the plunger length
# of Images Taken: Multiple (+10)

Figure 20:
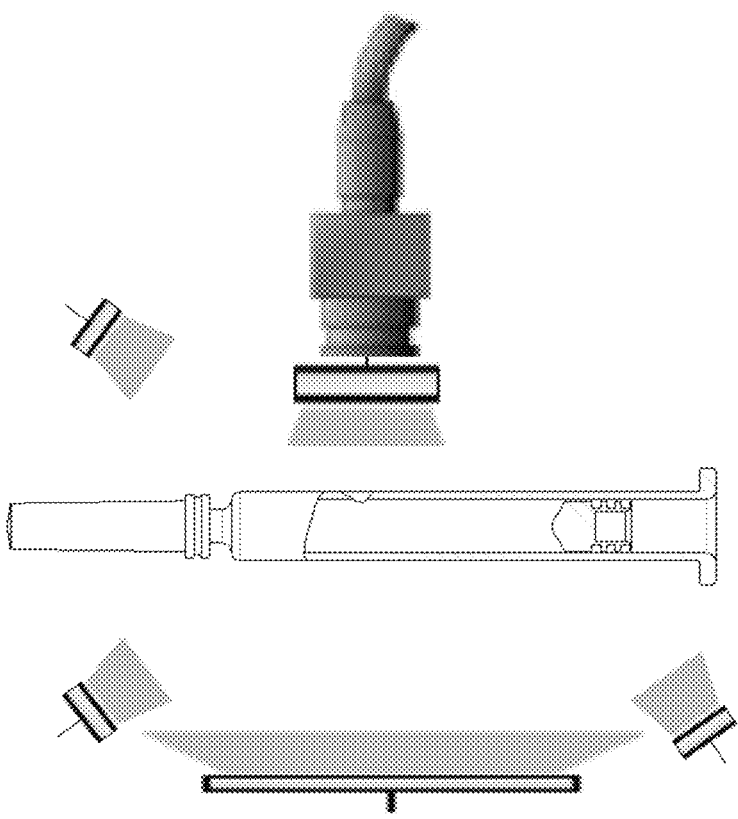
FIG. 20 illustrates a colored solution inspection configuration according to an embodiment of the present invention.

FIG. 20 illustrates a camera configuration for inspecting the body of the syringe to identify the color of the solution inside the syringe (Step 36, Table 1). The configuration settings used are:
Camera: 12 MP (Monochrome)
Illumination: Backlight (ON,Strobe), Front Light (OFF), Rear Angled (OFF), Front Angled (OFF)
Field of View: 1× the syringe barrel length
# of Images Taken: 1

Figure 21:
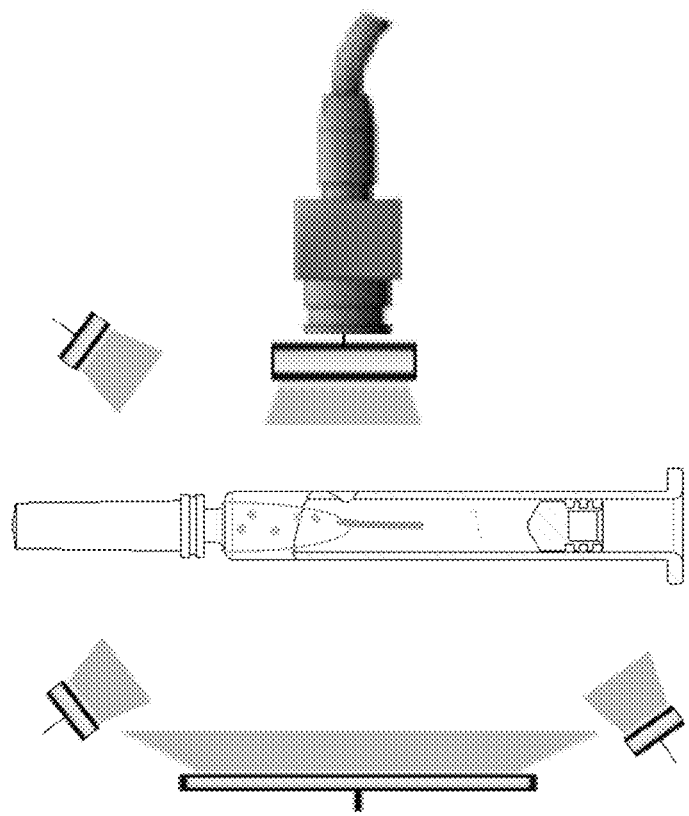
FIG. 21 illustrates a particles light reflection inspection configuration with subtraction after inversion according to an embodiment of the present invention.

FIG. 21 illustrates a camera configuration for inspecting the body of the syringe to identify moving light-reflecting particles on the syringe with a subtraction after inversion (Step 38, Table 1). The configuration settings used are:
Camera: 12 MP (Monochrome)
Illumination: Backlight (ON,Strobe), Front Light (OFF), Rear Angled (ON,Strobe), Front Angled (OFF)
Field of View: 1× the syringe barrel length
# of Images Taken: Multiple (+10)

Figure 22:
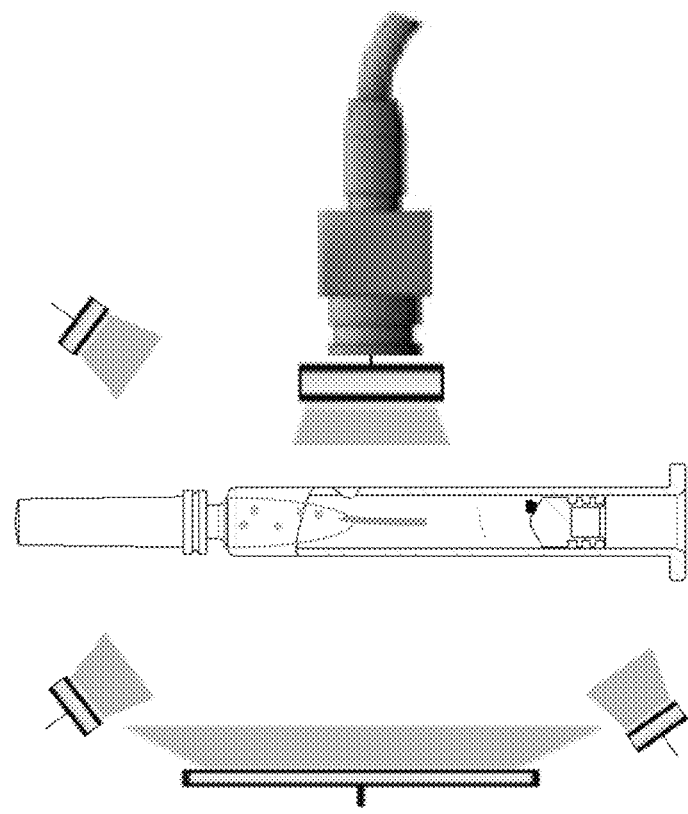
FIG. 22 illustrates a light reflecting body inspection configuration according to an embodiment of the present invention.

FIG. 22 illustrates a camera configuration for inspecting the body of the syringe with spin and light reflection to identify a crack on barrel, and airline, a chipped barrel scratched barrel, dirt or stain and a bruise (Step 39, Table 1). The configuration settings used are:
Camera: 12 MP (Monochrome)
Illumination: Backlight (OFF), Front Light (OFF), Rear Angled (ON,Strobe), Front Angled (OFF)
Field of View: 1× the syringe barrel length
# of Images Taken: Multiple (+10)

Figure 23:
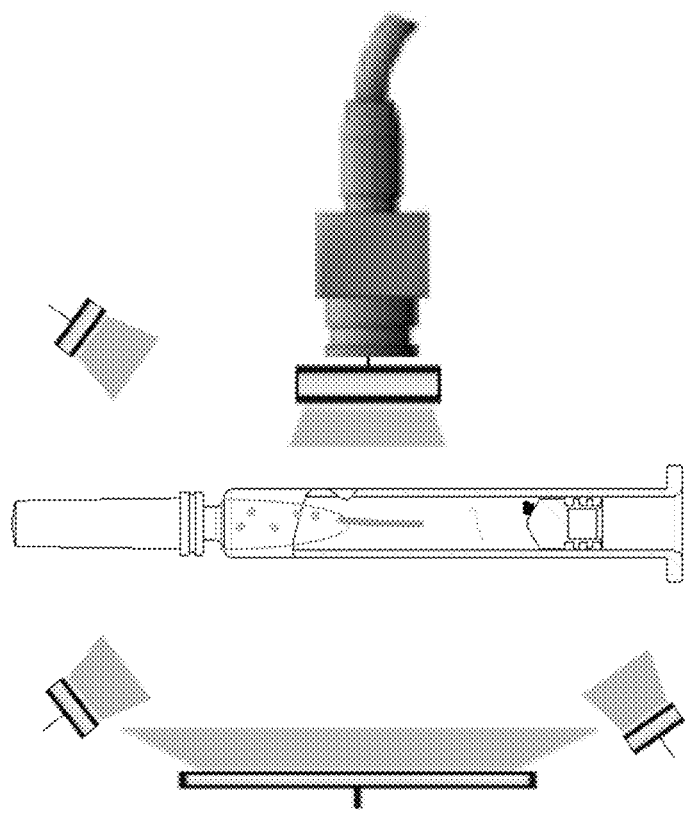
FIG. 23 illustrates a low reflecting particle on glass and floating particle inspection configuration with high speed according to an embodiment of the present invention.

FIG. 23 illustrates a camera configuration for inspecting the body of the syringe with a high spin and light reflection to identify particles on the glass wall of the syringe and floating particles (Step 40, Table 1). The configuration settings used are:
Camera: 12 MP (Monochrome)
Illumination: Backlight (OFF), Front Light (OFF), Rear Angled (ON,Strobe), Front Angled (OFF)
Field of View: 1× the syringe barrel length
# of Images Taken: Multiple (+10)

Figure 24:
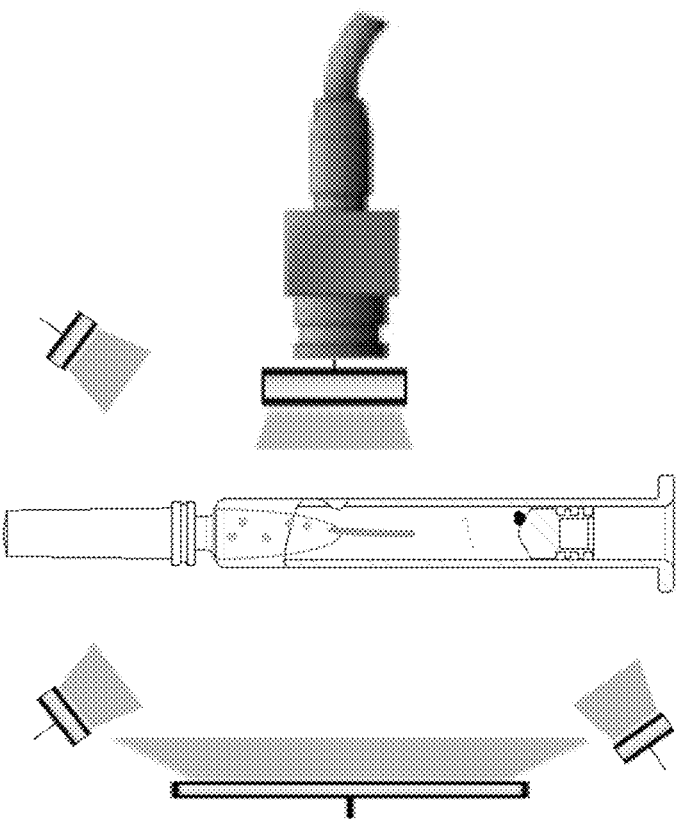
FIG. 24 illustrates a particle reflecting inspection configuration with subtraction after spinning and stop according to an embodiment of the present invention.

FIG. 24 illustrates a camera configuration for inspecting the body of the syringe with spinning and a subtraction after stopping to identify moving light-absorbing particles (Step 41, Table 1). The configuration settings used are:
Camera: 12 MP (Monochrome)
Illumination: Backlight (OFF), Front Light (OFF), Rear Angled (ON,Strobe), Front Angled (OFF)
Field of View: 1× the syringe barrel length
# of Images Taken: Multiple (+10)

Figure 25:
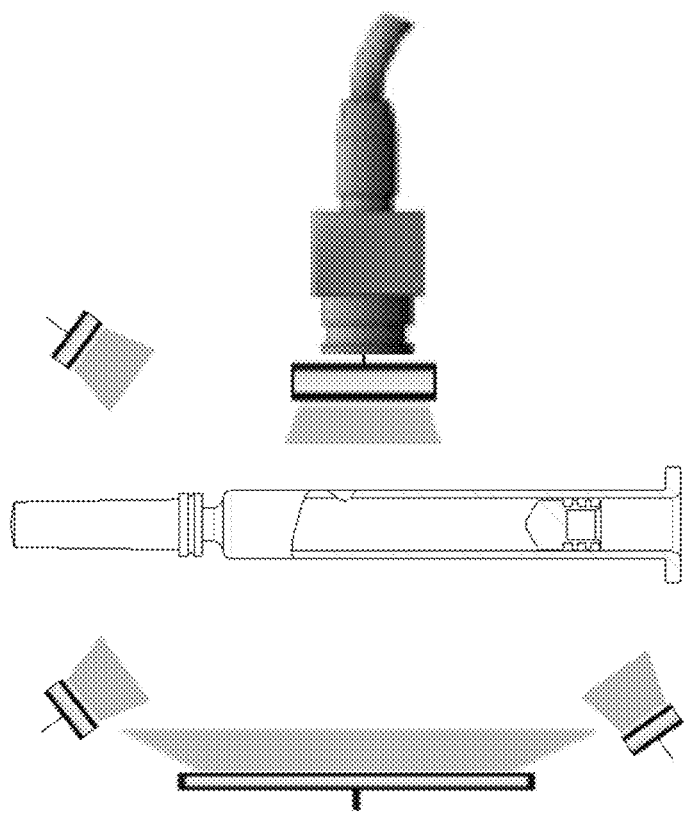
FIG. 25 illustrates a turbidity inspection configuration according to an embodiment of the present invention.

FIG. 25 illustrates a camera configuration for inspecting the body of the syringe to identify the turbidity on a solution of the syringe (Step 42, Table 1). The configuration settings used are:
Camera: 12 MP (Monochrome)
Illumination: Backlight (OFF), Front Light (OFF), Rear Angled (OFF), Front Angled (ON,Strobe)
Field of View: 1× the syringe barrel length
# of Images Taken: 1

Figure 26:
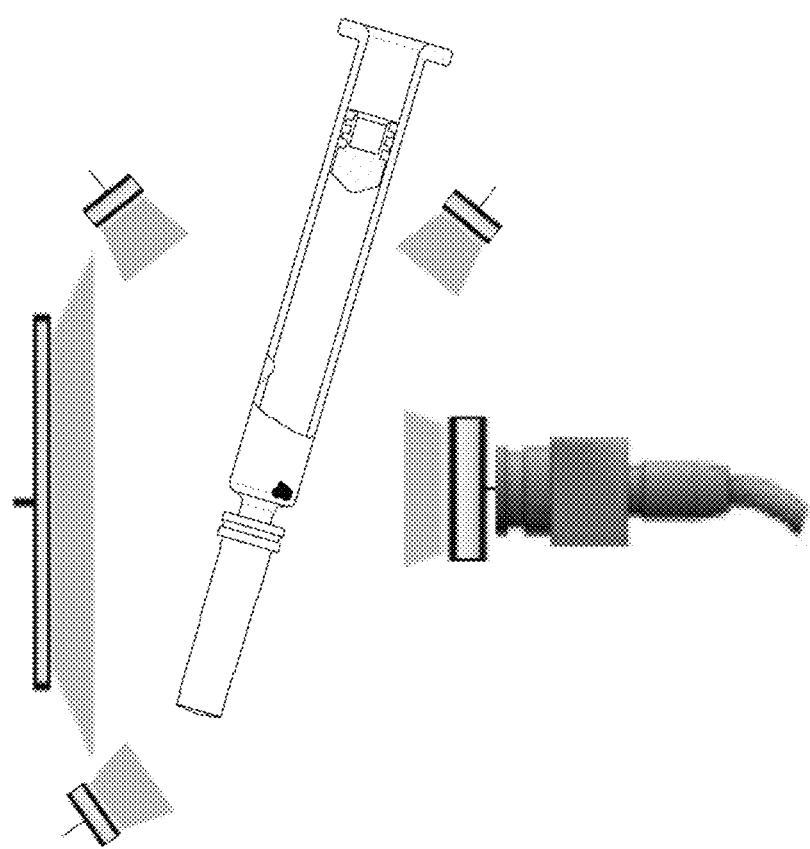
FIG. 26 illustrates a shoulder inspection configuration with tilt and spin according to an embodiment of the present invention.

FIG. 26 illustrates a camera configuration for inspecting the shoulder of the syringe with the needle down and the syringe tilted to identify cracks on the shoulder, a chipped shoulder and particles attached to the wall (Step 44, Table 1). The configuration settings used are:
Camera: 12 MP (Monochrome)
Illumination: Backlight (ON,Strobe), Front Light (OFF), Rear Angled (OFF), Front Angled (ON,Strobe)
Field of View: 1× the syringe barrel length
# of Images Taken: Multiple (+10)

The inspection system of the present invention preferably operates with $120V_{AC}$ or $240V_{AC}$ at 60 Hz with a process speed of 20-30 upm (units per minute). Nested tubs (BD and/or OMPI—10×16, 12×12 10×10, 8×8) are used as infeed to the system and Nested tub and/or Rondo tray (BD and OMPI, or Rondo) are used as outfeed from the system.

A Machine Vision Station is also provided with configurable software having the capability for Deep Learning & Conventional Vision Tools (i.e., COGNEX VIDi/VisionPro or Halcon 18.11+). Digital cameras are provided with lens and a field of view providing a pixel resolution of 25 μm/Pixel or smaller, where Camera-Link and/or GigE are used as camera interfaces. In addition, the light sources used provide LED visible light with an intensity up to 10,000 lux. A vision processor that can be provided as a separate module or as part of a computer or controller has the following preferred specifications: CPU: i7 (minimum), GPU: NVIDIA P5000, FRAME GRABBER: Camera-Link and/or GigE, STORAGE: 500 GB SSD, 10 TB HDD, and I/O Card: 24 $V_{DC}$.

According to an embodiment of the invention, the inspection system provides multiple access levels according to a user responsibility.

Level 1: The user is familiar with the regular operation of the system and has the required access to the HMIs in order to properly operate the equipment, access for viewing data and perform operations (Operators, Manufacturing-Associates).

Level 2: This user ensures optimal functionality of the system, having full access and full control over the equipment controls (HMI). Performs regular operation and troubleshooting of the system but does not have access to modifying recipe parameters (Advanced Operators, Mechanics).

Level 3: This user has access to all machine Validation Modes, Test Mode, HMI's, PLC's, etc. needed to validate the system (Supervisors, Maintenance, and Validations).

Level 4: This user ensures optimal functionality of the system, having full access and full control over the equipment controls (HMIs, PLC's, etc). The user is familiar the regular operation and troubleshooting of the system and has access to modifying inspection parameters (System Owners, Engineers).

Level 5: This user is responsible for installing, modifying, and troubleshooting the applications of the system/equipment following applicable procedures (Administrator).

The inspection system of the invention functions in various operating modes as will be explained below.

Production Mode—Deep Learning Inspection: In this mode, the machine runs in an auto-mode inspecting with Deep Learning Model(s) previously generated (under version control). This mode does not require operator confirmation. The machine must display current inspection data from the batch in process and saves a report upon conclusion of batch. The data stored in this mode must be associated to a batch number and is secured information. The report generated must be associated to a batch number. This mode shall not allow access to any critical process parameters.

Production Mode—Supervised: In this mode, the machine assists the operator by performing automatic inspection of the syringe unit and displaying the inspected digital images of the unit on-screen for the operator to confirm the results. The machine must display current inspection data from the batch in process and saves a report upon conclusion of batch. The data stored in this mode must be associated to a batch number and is secured information. The report generated must be associated to a batch number. This mode shall not allow access to any critical process parameters.

Production Mode—Supervised+Image Labelling & Storage: This mode performs the same operations as "the Production Mode—Supervised", but with the option to label the images with a defect category and store them in a corresponding folder. The system provides the option to enable/disable "Image Labeling & Storage".

Development Mode: This mode provides the flexibility to create development recipes and adjust product recipe parameters for characterization purposes. The inspection stations used in this mode are configurable from the development recipe. The machine stores and provides a test report upon conclusion of any test run. The report is associated to a Test Number and is segregated from production data. The system allows to save the development recipes but are not be available in production mode until validated. The system provides a selectable feature to mark the recipe as validated and make it available in Production Mode. The system has the capability to store images and inspection data for further evaluation and reference.

Maintenance Mode: This mode provides access to screens and functions required to complete maintenance tasks and does not allow any changes to the validated inspection process parameters.

FIGS. 1-3 illustrate the inspection station according to a preferred embodiment of the invention. The station has a booth arrangement of 54"L×36"D and a table height of 30"-36". The operator can sit or stand at the booth and access HMI and Infeed/Outfeed at ergonomic reach, where NEST Infeed is achieved from Operator in a sitting/standing position and RONDO Loading & Un-loading is achieved from the operator in a sitting/standing position. The station is configurable for Standalone Operation/Feeding (FIG. 2) or is connected to a Material Highway 20, as shown in FIG. 3. To provide auto-loading for RONDO Trays an Infeed Conveyor is added to continuously feed RONDO Trays. Also, the inspection station is connected to a material highway 20 for auto-infeed 22 for NEST. For auto-outfeed for RONDO Trays the inspection station outfeed 19 is connected to a material highway 20/21.

The inspection station provides a variety of safety features for OSHA compliance, including Lock-Out/Tag-Out capability. The system includes Lock-out and Tag-out provisions with manual lockable disconnect on electrical the cabinet and a pneumatic dump valve.

The lockout device is key operated or is able to be padlocked in an 'off' condition. At least one E-Stop is located at the operator areas and easily accessible points to allow stopping the equipment under unsafe conditions. The activation of E-Stops disables the electrical supply to the output modules, but PLC must remain energized to maintain logic control and information on the HMI. The equipment is fitted with access doors having safety interlocks integrated into the E-stop circuit.

The inspection station according to a preferred embodiment, has exposed frame parts made of stainless steel AISI 304 and/or 6061-T6 Aluminum (Anodized). The internal frame parts are paint-coated steel. The electrical cabinets and control boxes are type AISI 304 stainless steel, IP-52 enclosures. The frame is resistant to cleaning agent: 70% Isopropyl Alcohol.

While this invention has been particularly shown and described with references to preferred embodiments thereof, it will be understood by those skilled in the art that various changes in form and details may be made therein without departing from the spirit and scope of the invention.

The invention claimed is:

1. A pre-filed syringe inspection station comprising:
a nest loading area configured to receive syringe nests carrying a plurality of pre-filed syringes;
a unit pickup area configured to receive said syringe nests outside said nest loading area;
an empty nest discharge area configured to receive empty syringe nests from said unit pickup area;
an end of arm tool coupled to a robot arm, said end of arm tool having a plurality of syringe holding units, wherein each syringe holding unit comprises a syringe holding element configured to grab the pre-filed syringes from the syringe nests located on said unit pickup area and a rotary element configured to rotate said pre-filed syringes;
at least one illumination source configured to selectively illuminate said pre-filed syringes during inspection;
at least one camera configured to take at least one image of said pre-filed syringes during inspection;
a control unit connected to said at least one illumination source, said at least one camera, said robot arm and said end of arm tool, wherein said control unit carries out an inspection sequence based on a type of the pre-filed syringes by selectively moving said robot arm and said end of arm tool, selectively actuating said at least one illumination source and said at least one camera to analyze said at least one image in order to determine if said pre-filed syringes pass or fail inspection;
a syringe rejection area configured to receive from said end of arm tool pre-filed syringes that failed inspection;
a separator area configured to receive from said end of arm tool pre-filed syringes that passed inspection; and
a rondo tray loading area configured to receive from the separator area said pre-filed syringes that pass inspection.

2. The pre-filed syringe inspection station according to claim 1, further comprising a user interface connected to said control unit.

3. The pre-filed syringe inspection station according to claim 1, further comprising at least one of: an automatic syringe nests infeed coupled to said nest loading area, an automatic rondo tray infeed coupled to said rondo tray loading area or an automatic rondo tray outfeed coupled to said rondo tray loading area.

4. A method for inspecting pre-filed syringes comprising:
loading syringe nests carrying a plurality of pre-filed syringes into a nest loading area of an inspection station;
loading empty rondo trays into a rondo tray loading area of said inspection station;
moving said loaded syringe nests into a unit pickup area located outside said nest loading area;
moving empty syringe nests from said unit pickup area into an empty nest discharge area;
grabbing the pre-filed syringes from the syringe nests located on said unit pickup area;
inspecting said pre-filed syringes by controlling a robot arm coupled to an end of arm tool to selectively move said pre-filed syringes into predetermined positions in relation to at least one illumination source and at least one camera, selectively controlling illuminating said pre-filed syringes with said at least one illumination source and selectively controlling taking at least one image of said illuminated pre-filed syringes with said at least one camera;
determining if said pre-filed syringes pass or fail inspection by analyzing said at least one image;
moving the pre-filed syringes that failed inspection into a syringe rejection area;
moving the pre-filed syringes that passed inspection into a separator area;
moving the pre-filed syringes that passed inspection from a separator area into said empty rondo trays; and
removing said rondo trays from the rondo tray loading area when said rondo trays are completely filled with the pre-filed syringes that passed inspection.

5. The method according to claim 4, wherein the syringe nests are loaded into said nest loading area by at least one of: manually or automatically and the rondo trays are removed from said rondo tray loading area by at least one of: manually or automatically.

6. The method according to claim 4, wherein the integrity of a flange of said pre-filed syringes is inspected prior to moving said pre-filed syringes into the unit pickup area.

7. The method according to claim 4, wherein the inspecting step and the determining step comprise controlling said robot arm and said end of arm tool to position said pre-filed syringes in a horizontal direction in relation to said at least one camera and:
i) controlling said end of arm tool to spin said pre-filed syringes while being illuminated with a backlight positioned behind said pre-filed syringes and taking said at least one image to determine a presence of light-absorbing particles; and
ii) controlling said end of arm tool to spin said pre-filed syringes while being illuminated with a rear light positioned at an angle in a rear part of said pre-filed syringes and being illuminated with a front light positioned at an angle in a front part of said pre-filed syringes and taking said at least one image to determine a presence of light-reflecting particles.

8. The method according to claim 4, wherein the inspecting step and the determining step comprise controlling said robot arm and said end of arm tool to flip said pre-filed syringes to induce movement of particles suspended in a fluid inside the pre-filed syringes, illuminating said pre-filed syringes with a backlight positioned behind said pre-filed syringes and taking said at least one image to determine a presence of moving light-absorbing particles.

9. The method according to claim 4, wherein the inspecting step and the determining step comprise controlling said robot arm and said end of arm tool to hold said pre-filed syringes static, illuminating said pre-filed syringes with a backlight positioned behind said pre-filed syringes and taking said at least one image to determine a distance from a plunger of said pre-filed syringes to a meniscus of a liquid inside said pre-filed syringes and a distance from said meniscus to a shoulder of said pre-filed syringes.

10. The method according to claim 4, wherein the inspecting step and the determining step comprise controlling said end of arm tool to spin said pre-filed syringes and illuminating said pre-filed syringes with a backlight positioned behind said pre-filed syringes and a front light positioned in front of said pre-filed syringes, and taking said at least one image to determine a condition of at least one of: a needle or a needle shield of said pre-filed syringes.

11. The method according to claim 4, wherein the inspecting step and the determining step comprise controlling said robot arm and said end of arm tool to position said pre-filed syringes with a needle facing up, spinning said pre-filed syringes while illuminating said pre-filed syringes with a backlight positioned behind said pre-filed syringes and a rear light positioned at an angle in a rear part of said pre-filed syringes, and taking said at least one image to determine at least one of: a condition of a body of said pre-filed syringes, a presence of particles on a glass wall of said body or a presence of particles floating on a liquid inside said pre-filed syringes.

12. The method according to claim 4, wherein the inspecting step and the determining step comprise controlling said end of arm tool to spin and stop said pre-filed syringes while illuminating said pre-filed syringes with a backlight positioned behind said pre-filed syringes and taking said at least one image to determine the presence of moving light-absorbing particles.

13. The method according to claim 4, wherein the inspecting step and the determining step comprise:
  i) controlling said end of arm tool to spin said pre-filed syringes while illuminating said pre-filed syringes with a backlight positioned behind said pre-filed syringes and a front light positioned in front of said pre-filed syringes, and taking said at least one image to determine a condition of a side of a plunger of said pre-filed syringes; and
  ii) controlling said robot arm and said end of arm tool to tilt and spin said pre-filed syringes while illuminating said pre-filed syringes with the backlight positioned behind said pre-filed syringes and a front light positioned at an angle in a front part of said pre-filed syringes and taking said at least one image to determine a condition of a top of the plunger of said pre-filed syringes.

14. The method according to claim 4, wherein the inspecting step and the determining step comprise controlling said robot arm and said end of arm tool to position said pre-filed syringes static with a needle facing up while illuminating said pre-filed syringes with a backlight positioned behind said pre-filed syringes and taking said at least one image to determine a color of a solution inside said pre-filed syringes.

15. The method according to claim 4, wherein the inspecting step and the determining step comprise controlling said robot arm and said end of arm tool to flip said pre-filed syringes between a needle up position and needle down position while illuminating said pre-filed syringes with a backlight positioned behind said pre-filed syringes and a rear light positioned at an angle in a rear part of said pre-filed syringes, and taking said at least one image to determine the presence of moving light-reflecting particles.

16. The method according to claim 4, wherein the inspecting step and the determining step comprise:
  i) controlling said end of arm tool to spin said pre-filed syringes while illuminating said pre-filed syringes with a rear light positioned at an angle in a rear part of said pre-filed syringes and taking said at least one image to determine at least one of: a condition of a body of said pre-filed syringes, a presence of particles on a glass wall of said body or a presence of particles floating on a liquid inside said pre-filed syringes; and
  ii) controlling said end of arm tool to spin and stop said pre-filed syringes while illuminating said pre-filed syringes with a rear light positioned at an angle in a rear part of said pre-filed syringes and taking said at least one image to determine the presence of moving light-absorbing particles.

17. The method according to claim 4, wherein the inspecting step and the determining step comprise controlling said robot arm and said end of arm tool to position said pre-filed syringes static while illuminating said pre-filed syringes with a front light positioned at an angle in a front part of said pre-filed syringes and taking said at least one image to determine a turbidity of a solution inside said pre-filed syringes.

18. The method according to claim 4, wherein the inspecting step and the determining step comprise controlling said robot arm and said end of arm tool to flip said pre-filed syringes with a needle down and tilting said pre-filed syringes while illuminating said pre-filed syringes with the backlight positioned behind said pre-filed syringes and a front light positioned at an angle in a front part of said pre-filed syringes and taking said at least one image to determine a condition of a shoulder of said pre-filed syringes.

19. The method according to claim 4, wherein the inspecting step and the determining step are carried out to determine at least one of: a condition of a flange of said pre-filed syringes, a presence of light-absorbing particles, a presence of light-reflecting particles, a presence of moving light-absorbing particles, a distance from a plunger of said pre-filed syringes to a meniscus of a liquid inside the pre-filed syringes, a distance from said meniscus of the liquid inside the pre-filed syringes to a shoulder of said pre-filed syringes, a condition of a needle of said pre-filed syringes, a condition of a needle shield of said pre-filed syringes, a condition of a body of said pre-filed syringes, a presence of particles on a glass wall of said pre-filed syringes, a presence of floating particles on a liquid inside said pre-filed syringes, a condition of a side of a plunger of said pre-filed syringes, a condition of a top of a plunger of said pre-filed syringes, a color of a solution inside said pre-filed syringes, a presence of light-reflecting particles, a turbidity condition of the solution inside said pre-filed syringes, or a condition of a shoulder of said pre-filed syringes.

* * * * *